US008859282B2

(12) United States Patent
Kale et al.

(10) Patent No.: US 8,859,282 B2
(45) Date of Patent: Oct. 14, 2014

(54) METHOD FOR PRESERVATION OF HUMAN HEMATOPOIETIC STEM OR PROGENITOR CELLS

(75) Inventors: Vaijayanti P. Kale, Pune (IN); Lalita S. Limaye, Pune (IN); Ashwini Hinge, Pune (IN); Avadhesha Surolia, Bangalore (IN)

(73) Assignees: Department of Biotechnology, New Delhi (IN); Indian Institute of Sciences, Bangalore (IN)

( * ) Notice: Subject to any disclaimer, the term of this patent is extended or adjusted under 35 U.S.C. 154(b) by 1772 days.

(21) Appl. No.: 12/096,292

(22) PCT Filed: Jun. 27, 2006

(86) PCT No.: PCT/IN2006/000215
§ 371 (c)(1),
(2), (4) Date: Oct. 24, 2008

(87) PCT Pub. No.: WO2007/066352
PCT Pub. Date: Jun. 14, 2007

(65) Prior Publication Data
US 2009/0305325 A1 Dec. 10, 2009

(30) Foreign Application Priority Data
Dec. 6, 2005 (IN) ................ 3284/DEL/05

(51) Int. Cl.
*C12N 5/02* (2006.01)
*C12Q 1/02* (2006.01)
*C12N 5/0789* (2010.01)

(52) U.S. Cl.
CPC ........ *C12N 5/0647* (2013.01); *C12N 2501/125* (2013.01); *C12N 2501/22* (2013.01); *C12N 2501/14* (2013.01)
USPC ............................ 435/374; 435/29

(58) Field of Classification Search
None
See application file for complete search history.

(56) References Cited

U.S. PATENT DOCUMENTS

| 5,780,447 A * | 7/1998 | Nienhuis ............ 514/44 R |
| 6,103,879 A * | 8/2000 | Chaovapong et al. ..... 530/388.1 |
| 2002/0169122 A1* | 11/2002 | Majumdar et al. ........ 514/12 |
| 2003/0049339 A1 | 3/2003 | Colucci et al. |
| 2004/0229206 A1 | 11/2004 | Moore |
| 2005/0260292 A1* | 11/2005 | Yang ................. 424/776 |
| 2006/0057634 A1* | 3/2006 | Rye ................... 435/7.1 |

OTHER PUBLICATIONS

Elias et al., "Cord Blood from Collection to Expansion: Feasibility in a Regional Blood bank", Indian Journal of Pediatrics, vol. 70, Apr. 2003, pp. 327-336.*
Caceres-Cortes et al., "Cytotoxic activity of *Justicia spicigera* is inhibited by bcl-2 proto-oncogene and induces apoptosis in a cell cycle dependent fashion", Phytotherapy Research, 2001, vol. 15, pp. 691-697.*
Yao et al. "A systematic strategy to optimize ex vivo expansion medium for human hematopietic stem cells derived from umbilical cord blood mononuclear cells", Experimental Hematology, 2004, vol. 32, pp. 720-727.*
Shinohara et al., "Elucidation of the mechanism enhancing the avidity of lectin with oligosaccharides on the solid phase surface", Glycobiology, 1997, vol. 7, No. 8, pp. 1207-1208.*

* cited by examiner

*Primary Examiner* — Laura Schuberg
(74) *Attorney, Agent, or Firm* — The Webb Law Firm

(57) ABSTRACT

Maintenance of quiescent hematopoietic stem and progenitor cells (HSPC) in culture without the addition of exogenous growth factors is an important aspect in clinical hematology. A recent report described the ability of Flt3 receptor-interacting lectin (FRIL) in the maintenance of cord blood (CB) derived progenitors in vitro. Since FRIL is a mannose binding lectin, the effectiveness of four such lectins of well-characterized specificities on the preservation of HSPC of CB origin have been examined. The HSPC preservation activity of lectins was assessed by in vitro colony forming unit (CFU) and long-term culture initiating cell (LTC-IC) assays. It was found that all four lectins had a HSPC preservation activity at least up to 30 days in culture without addition of exogenous growth factors. The results indicate that use of such lectins may provide a cost effective method of HSPC maintenance for clinical use.

11 Claims, 4 Drawing Sheets

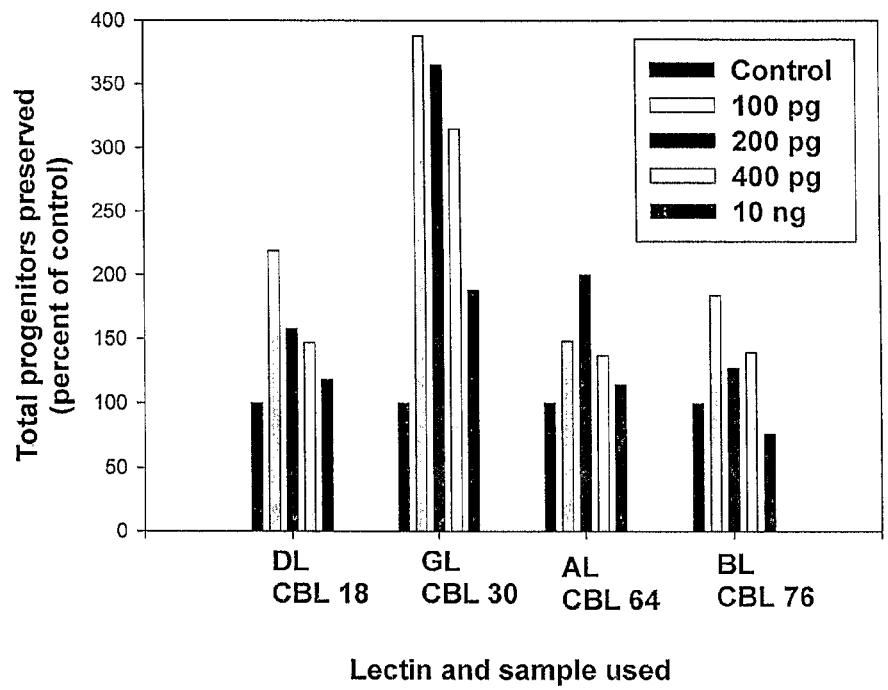

Fig 1: Mannose specific lectins DL, GL, AL and BL preserve HSPC for 10 days in liquid culture. CD34[+] cells were incubated with various concentrations of lectins as indicated and the cells were then subjected to CFU assays. The colonies were scored for the presence of CFU-GM, CFU-GEMM and BFU-E. The data represented in this figure are expressed as total progenitors preserved as percent of control cells.

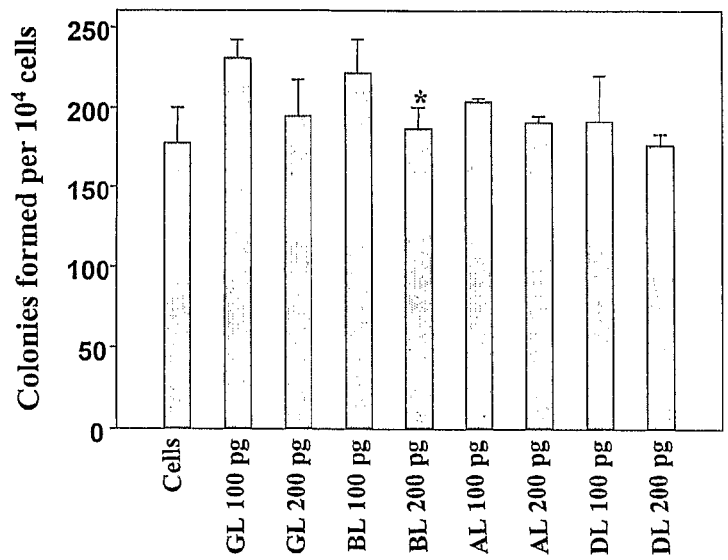
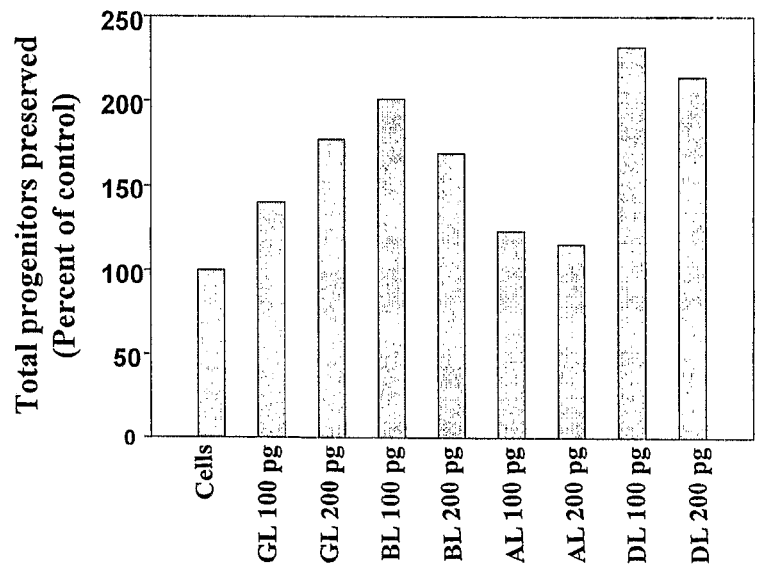
Fig 2: Comparative efficacy of GL, BL, AL and DL on $CD34^+$ cells isolated from the same sample. A: CFU generated /$1 \times 10^4$ $CD34^+$ cells after 10 days incubation with or without lectins B: Total number of progenitors preserved expressed as percent of control.

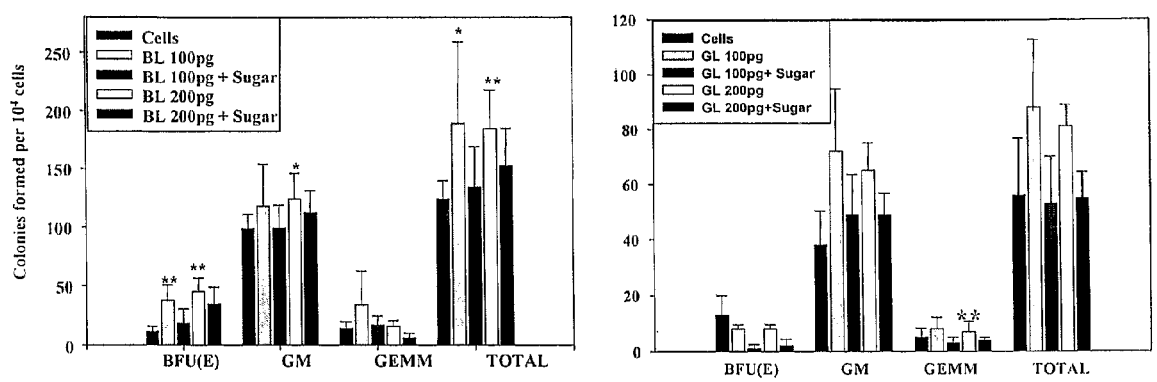

Fig 3: Specificity of lectin action: Use of specific sugar Methyl α Mannoside (20mM) in the incubation medium along with lectin abrogates the preservation effect. $CD34^+$ cells were incubated with or without lectins for 10 days in the presence of absence of 20 mM Methyl α Mannoside. The recovered cells were subjected to standard colony formation assays and the colonies were scored at 14 days.
A: Experiment with BL.  B: Experiment with GL (* p≤0.05 ** p ≤ 0.001)

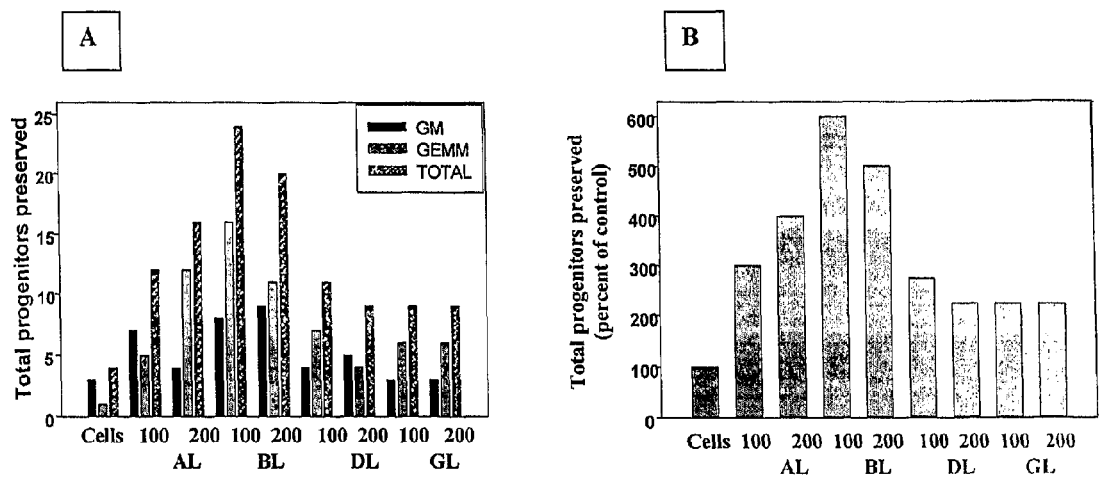

Fig 4: AL, BL, DL and GL preserve primitive cells giving rise to LTC-IC. $CD34^+$ cells were incubated for 30 days with 100 and 200 pg/ml of all lectins and the surviving cells were seeded on irradiated M210B4. The cultures were maintained for 5 weeks by demi-defoliation. Both adherent and non-adherent cells were pooled and assayed for colony formation.

A: Total number of LTC-IC preserved in $CD34^+$ cells incubated with AL, BL, DL and GL for 30 days of incubation.
B: Data in A expressed as percent of control.

METHOD FOR PRESERVATION OF HUMAN HEMATOPOIETIC STEM OR PROGENITOR CELLS

FIELD OF INVENTION

This invention relates to a method for preservation of Human hematopoietic stem or progenitor cells.

More particularly, it relates to a method for preservation of Human hematopoietic stem or progenitor cells with the effect of mannose binding lectins on human hematopoietic stem/progenitor cells.

BACKGROUND OF THE INVENTION

Preservation of hematopoietic stem/progenitor cells (HSPC) is conventionally carried out using low temperature freezing either at $-80°$ C. (mechanical freezers) or at $-196°$ C. (liquid nitrogen) and it is altogether a separate science in itself. Present invention relates to maintenance of HSC in culture. Maintenance HSPC in vitro without proliferation or differentiation has important clinical applications. Techniques such as in vitro purging of tumor cells using culture techniques or by use of chemotherapeutic agents necessitates that the HSPC remain unaffected in the culture. In genetic engineering protocols it could be advantageous to eliminate all the short-lived progenitors, which are growth factor dependent and then use the surviving primitive cells for transduction purposes. Thus a search for agents which can maintain the HSPC in culture and identification of signals involved in maintenance of the quiescent state is likely to form a fruitful endeavor. Earlier efforts in this direction to maintain HSPC in culture have been made using either specific matrix molecules like denatured collagen (Mauney et al, 2004 Biomaterials, 25, 16: 3233-43; Kim et al 2003, Int J Hematol; 78, 2:126-32; Banu et al 2001, Cytokine. 21; 13, 6:349-58) or growth factors like FLT3L (Shapiro et al 1996, Hemather; 5, 6:655-62) or hematopoietic growth factors like Epo (Eridani et al 1998, Biotherapy 10, 4:295-8). These approaches, however, involve use of expensive reagents. The cost factor becomes a major issue when it is to be applied to clinical set ups especially in developing countries. Recently, a lectin named Flt3 receptor-interacting lectin (FRIL) was shown to preserve the quiescent HSPC derived from cord blood (CB) in culture for 30 days without the change of medium and without the exogenous addition of growth factors. (Colucci, G. et al 1999 Proc. Natl. Acad. Sci. USA 96, 646-650; Kollet O. et al 2000 Expt. Hematol. 28, 726-736.) The plant lectin FRIL was shown to support prolonged in vitro maintenance of quiescent, human cord blood CD 34 (+) CD38 (−/low)/SCID repopulating stem cells. It is reported that this maintenance of quiescent CB progenitors may be through the cell cycle modulation through HTm4 and HTm4S (Xie, X. Y., Xie C., Shi, W., Li, J., Li, Y. H., Wang, D. M., Bai, C. X., Chen, L. & Pei, X. T. 2004 56, 306-312).

Since FRIL is a mannose binding lectin, screening for more mannose binding lectins have been done for their possible HSPC preservation activity so that they can also be used as tools to identify the signals involved in maintenance of quiescent HSPC. Thus the present invention has two distinct advantages over earlier approaches, one of being cost effective and the second of providing useful and specific reagents to study signaling mechanisms.

Maintenance of HSPC in culture has a great clinical utility especially if it can be done without change of medium or use of expensive reagents. The present invention provides a method to achieve this. The mannose specific lectins that have been used in the present study showed HSPC preservation activity up to 30 days without growth factor addition or medium change providing a cost effective method to preserve HSPC in culture.

OBJECTS OF THE INVENTION

An object of the present invention is to provide a method for preservation of Human hematopoietic stem/progenitor cells.

Another object of the present invention is to provide a method for preservation of Human hematopoietic stem/progenitor cells with the effect of mannose binding lectins on human hematopoietic stem/progenitor cells.

Still another object of the present invention is to provide a cost effective method for preservation of Human hematopoietic stem/progenitor cells by using lectins.

SUMMARY OF THE INVENTION

According to this invention there is provided a method for preservation of Human hematopoietic stem/progenitor cells, wherein the said method comprising the step of:
a) providing the purified lectins from the group consisting of *Dolichos lablab* lectin (DL), Garlic lectin (GL), *Musa paradisica* (BL), *Artocarpus integrifolia* (AL) etc. by dialyzing against phosphate buffered saline (10 mM, pH7.4) followed by filtration through 0.2 a filters followed by protein determination by using micro BCA kit to check protein loss;
b) isolating the $CD34^+$ cells from human cord blood sample;
c) incubating the isolated $CD34^+$ cells obtained from step (b) with different concentration of lectins ranges between 100 pg/ml to 10 ng/ml for a period 10 to 30 days followed by toxicity test;
d) subjecting incubated $CD34^+$ cells obtained from step (c) to CFU assay or seeding on irradiating M210B4 feeders for LTC-IC assays;
e) interpreting the effect of lectins on human hematopoietic stem/progenitor cells preservation.

BRIEF DESCRIPTION OF ACCOMPANYING FIGURES

FIG. 1 represents Mannose specific lectins DL, GL, AL and BL preserve HSPC for 10 days in culture. $CD34^+$ cells were incubated with various concentrations of lectins as indicated and the cells were then subjected to CFU assay. The colonies were scored for the presence of CFU-GM, CFU-GEMM and BFU-E. The data represented in this figure are expressed as total progenitors preserved as percent of control cells.

FIG. 2 represents comparative efficacy of GL, BL, AL and DL on $CD34^+$ cells isolated from the same sample. A: CFU generated per $1\times10^4$ $CD34^+$ cells after 10 days incubation with or without lectins B: Total number of progenitors preserved expressed as percent of control.

FIG. 3 represents specificity of lectin action: Use of specific sugar Methyl∝Mannoside (20 mM) in the incubation medium along with lectin abrogates the preservation effect. $CD34^+$ cells were incubated with or without lectins for 10 days in the presence or absence of 20 mM Methyl∝Mannoside. The recovered cells were subjected to standard CFU assay and the colonies were scored at 14 days. A: Experiment with BL. B: Experiment with GL ($*p \leq 0.05**p \leq 0.001$)

FIG. 4 represents effect of AL, BL, DL and GL in preservation of primitive cells giving rise to LTC-IC. $CD34^+$ cells were incubated with 100 and 200 pg/ml of AL, BL DL and GL independently and then seeded on irradiated M210B4. The cultures were maintained for 5 weeks by weekly demi-defoliation. Both adherent and non-adherent cells were pooled and assayed for colony formation.

A: Total number of LTC-IC preserved in CD34$^+$ cells incubated with AL, BL, DL and GL after 30 days of incubation.

B: Data in A expressed as percent of control.

DETAILED DESCRIPTION OF THE INVENTION

Ex vivo preservation of hematopoietic stem and progenitor cells without the addition of growth factors and without the change in medium may be of immense use in various clinical and experimental set ups. Such incubation in culture media may be required for in vitro purging of tumor cells without affecting the quiescent HSPC. It may also help in removal of factor dependent differentiated cells leaving behind primitive HSPC, which can be used for further manipulations including genetic engineering.

In the present invention, some of the mannose binding lectins of defined specificities have been examined for their preservation effect on CD34$^+$ cells isolated from cord blood. It has been observed that these lectins indeed have a HSPC preservation activity for up to 30 days without change of medium and without addition of growth factors as assessed by CFU and LTC-IC assays. The optimal concentration for all lectins ranged from 100-200 pg/ml. Since the binding specificities of these lectins are well characterized (Singh, D. D. and Surolia, A. and Vijayan, M. 2004 Acta Crystallographica D60, 2104-2106) so these lectins can be used as specific and well-defined tools in signal transduction studies.

Accordingly the present invention provides a method for preservation of Human hematopoietic stem/progenitor cells, wherein the said method comprising the step of:
a) providing the purified lectins from the group consisting of *Dolichos lablab* lectin (DL), Garlic lectin (GL), *Musa paradisica* (BL), *Artocarpus integrifolia* (AL), etc. by dialyzing against phosphate buffered saline (10 mM, pH 7.4) followed by filtration through 0.2µ filters followed by protein determination by using micro BCA kit to check protein loss;
b) isolation of CD34$^+$ cells from human cord blood sample;
c) incubation of the isolated CD34$^+$ cells obtained from step (b) with different concentration of lectins ranges between 100 pg/ml to 10 ng/ml for a period 10 to 30 followed by toxicity test;
d) subjecting incubated CD34$^+$ cells obtained from step (c) to CFU assay or seeding on irradiating M210B4 feeders for LTC-IC assays;
e) interpreting the effect of lectins on hum an hematopoietic stem/progenitor cells preservation.

In an embodiment of the present invention, lectins used are selected from the group consisting of *Dolichos lablab* lectin (DL), garlic lectin (GL; *Allium sativum* isolectin II, viz. ASAII), *Musa Paradisica* (BL) and the mannose binding lectin from *Artocarpus integrifolia* (artocarpin) are purified according to the procedures described in Singh et al (2004 Acta Crystallographica D60, 2104-2106), Mo et al (2001 Eur. J. Biochem. 268, 2609-2615), Dam et al (1998 J. Bio. Chem. 273, 5528-5535) and Misquith et al (1994 J. Biol. Chem. 269, 30393-30401).

In another embodiment of the present invention, the homogeneity of purified lectins is confirmed by SDS-polyacrylamide gel electrophoresis.

In yet another embodiment of the present invention, lectins are dialyzed against phosphate buffer saline and filtered through 0.2 to 0.4µ filters.

In still another embodiment of the present invention, protein content is determined by using micro BCA kit to check protein loss and aliquots are kept at 2-8° C.

In yet another embodiment of the present invention, Human cord blood is taken from local hospitals after obtaining informed consent of the mother.

In yet another embodiment of the present invention, human cord blood sample (40 to 100 ml depending upon the sample) is collected in sterile bottle containing 40 IU of heparin as an anticoagulant per ml of plain culture medium (IMDM, DMEM, RPMI-1640 etc).

In yet another embodiment of the present invention, Red blood cells (RBCs) are separated from mononuclear cells (MNC) by mixing HES (1 ml; Sigma, hetastarch 6% solution in 0.9% NaCl) and cord blood (1-4 ml).

In yet another embodiment of the present invention, suspending the MNC obtained from cord blood by HES separation as described above in isolation buffer (0.6% Na-citrate and 2% BSA in 10 mM PBS, pH7.4) and isolating the CD34$^+$ cells from MNC by immuno-magnetic separation (Dynal) as per the manufacturer's instructions.

In yet another embodiment of the present invention, the isolated CD34$^+$ cells are incubated with different concentration of lectins ranges between 100 pg/ml to 10 ng/ml for a period of 10 to 30 days.

In yet another embodiment of the present invention, concentration range of lectins used is in the range between 10 pg/ml to 80 ng/ml for performing toxicity test on TF1 cells using MTT or XTT assays.

In yet another embodiment of the present invention, no cytotoxicity is observed in lectin preparations up to 80 ng/ml.

In yet another embodiment of the present invention, CD34$^+$ cells were incubated with lectins for various time periods ranging from 10 to 30 days and were subjected to CFU assay or were seeded on irradiated M210B4 feeders for LTC-IC assay.

In yet another embodiment of the present invention, the incubated CD34$^+$ cells were tested for the number of progenitors preserved by scoring for different types of colonies (such as BFU-E, CFU-GM and CFU-GEMM) formed in a semi-solid methylcellulose medium (Methyl cellulose 1%+Plain IMDM 70 ml+Human FCS 30%+Na-Pyruvate 10 µM+Iron saturated Transferrin 0.036%+β Mercapto ethanol $5 \times 10^{-5}$ M+BSA 1%) containing standard growth factors qualified for human clonogenic cells such as hSCF 20 ng/ml, GM-CSF—2 ng/ml, IL3 4 ng/ml and Epo 21 U/ml. The CFU assay gives an estimate of different types of progenitors present in a test population.

In yet another embodiment of the present invention, the total numbers of progenitors preserved by lectins were calculated by normalizing with the number of cells recovered after incubation with lectins for various time periods.

If "x" is the number of colonies obtained from $1 \times 10^5$ cells (recovered after incubation with lectins for specified period) in CFU assay and "y" is the total number of recovered cells then the "absolute number of progenitors preserved" becomes $xy/1 \times 10^5$ In yet another embodiment of the present invention, the incubated CD34$^+$ cells were optionally seeded on irradiated (8000 rads) M210B4 feeder layer formed on collagen-coated wells using Myelocult medium (Stem Cell Technology, Canada) followed by maintaining the culture for 5-6 weeks by weekly demi-defoliation.

In yet another embodiment of the present invention, the said cultures were harvested by trypsinization.

In an embodiment of the present invention, adherent (feeder layer and the hematopoietic cells closely associated with it) and non adherent (floating hematopoietic cells) populations are pooled from harvested cultures to assay for colony formation.

The following examples are given by the way of illustration and therefore should not be construed to limit the scope of the present invention.

EXAMPLE 1

Purification of Lectins:

In the present invention lectins were used namely, *Dolichos lablab* (DL), Banana lectin (BL) and *Artocarpus integrifolia* lectin, artocarpin (AL) and garlic lectin (GL). They were purified and characterized as follows.

Lectins from *Dolichos lablab* lectin (DL), garlic lectin (GL; *Allium sativum* isolectin II, viz. ASAII), *Musa Paradisica* (BL) and the mannose binding lectin from *Artocarpus integrifolia*; artocarpin (AL) were purified following the procedures described in Singh et al (2004 Acta Crystallographica D60, 2104-2106; Mo et al. (2001, Eur. J. Biochem. 268, 2609-2615; Dam et al. (1998, J. Bio. Chem. 273, 5528-5535) and Misquith et al (1994, J. Biol. Chem. 269, 30393-30401) Homogeneity of the purified lectins was confirmed by SDS-polyacrylamide gel electrophoresis (Laemmli, U. K. 1970 Nature 277, 680-685).

The lectin preparations were dialyzed extensively against phosphate buffered saline and filtered through 0.2-micron filters. Protein content was determined using micro BCA kit and aliquots were kept at 4° C. The protein determination was frequently done to check protein loss, if any.

EXAMPLE 2

Isolation of $CD34^+$ Cells from Human Cord Blood:

Cord blood was collected from local hospitals after obtaining informed consent of the mother. The protocols described in these studies were approved by the Institutional Ethics Committee. In brief, cord blood was collected in a sterile bottle containing heparin (40 IU of heparin/ml of plain medium) and processed soon thereafter by using standard protocols. Red blood cells (RBCs) were separated by HES (4 ml of blood:1 ml of HES) and mononuclear cell (MNC) fraction was isolated by density gradient (Histopaque, Sigma) using standard protocols. MNCs were suspended in isolation buffer and $CD34^+$ cells were isolated by immunomagnetic separation (Dynal) as per the manufacturer's instructions.

EXAMPLE 3

Functional Assays for Determination of HSPC Activity:

Isolated $CD34^+$ cells were incubated with different concentrations (100 pg/ml to 10 ng/ml for all four lectins) of lectins for various time periods (10 to 30 days). This concentration range of lectins used was predetermined by carrying out toxicity tests on TF 1 cells using MTT or XTT assays. The $CD34^+$ cells incubated for various time periods were subjected directly to CFU assay or seeded on irradiated M210B4 feeders for LTC-IC assays as described below. $CD34^+$ cells without addition of lectin were kept as control in each experiment performed.

(a) Colony Forming Unit (CFU) Assay:

$CD34^+$ cells incubated for various time periods with the lectins were tested for the number of progenitors preserved by scoring for the different types of colonies (BFU-E, CFU-GM and CFU-GEMM) formed in a semisolid methylcellulose medium containing standard growth factors qualified for human clonogenic cells (hSCF 20 ng/ml, GM-CSF-2 ng/ml, IL3 4 ng/ml and Epo 2 IU/ml) using standard criteria (Eaves C and Lambi K (1995) Atlas of Human Hematopoietic colonies. Stem Cell Technologies, Vancouver, Canada). This assay formed a primary screen for the lectins and the optimal concentrations of lectins giving good results in this system were used for long-term assays.

(b) Long Term Culture Initiating Cell (LTC-IC) Assays:

This assay gives an estimate of more primitive HSPC present in the test population than those scored by CFU assays (Sutherland et al 1989 Blood 74: 1563-1570). The $CD34^+$ cells incubated with various concentrations and periods as indicated in the results were seeded on irradiated (8000 rads) M210B4 feeder layer formed on collagen coated wells using Myelocult medium. The cultures were maintained for 5-6 weeks by weekly demi-defoliation. The cultures were then harvested by trypsinization. Both adherent and non-adherent populations were pooled and assayed for colony formation.

EXAMPLE 4

Determination of Optimal Concentration of Lectins for HSPC Preservation:

We selected the range of various lectins based on the cytotoxicity assay earned on TF 1 cells. We observed that the lectin preparations did not show any cytotoxicity up to 80 ng/ml concentration (data not shown). It was, however, necessary to determine the optimal concentration of the various lectins to be used in the context of their HSPC preservation ability. In order to achieve this we incubated the $CD34^+$ cells for a fixed time interval of 10 days with different concentrations of lectins (from 100-400 pg/ml and 10 ng/ml). After incubation cells were subjected to CFU assays as described. Numbers of total progenitors preserved were calculated from the number of colonies formed from recovered cells after incubation with lectin(s). It was observed that all lectins namely AL, BL, DL and AL preserved the progenitors at least up to 10 days of incubation without any medium changes as well as without any cytokine supplementation (FIG. 1). Lower concentrations of all lectins (in the range of 100 pg/ml and 200 pg/ml) were found to be optimal in the context of the preservation of HSPC in several experiment (N=10) and, therefore, these concentrations were used in further experiments.

TABLE 1

Determination of Optimal Concentration of Lectins

| Lectin used | Cells | Total progenitors preserved after 10 days of incubation by | | | |
|---|---|---|---|---|---|
| | | 100 pg/ml | 200 pg/ml | 400 pg/ml | 10 ng/ml |
| AL | 357 | 528 | 717 | 489 | 408 |
| BL | 579 | 1064 | 734 | 806 | 441 |
| DL | 3294 | 7233 | 5231 | 4855 | 3908 |
| GL | 495 | 1925 | 1808 | 1562 | 931 |

TABLE 2

Total Progenitors Preserved By Lectins Expressed As Percent of Control

| Lectin Used | Cells | Total progenitors preserved by lectins Expressed as percent of control | | | |
|---|---|---|---|---|---|
| | | 100 pg/ml | 200 pg/ml | 400 pg/ml | 10 ng/ml |
| AL | 100 | 148 | 201 | 137 | 114 |
| BL | 100 | 184 | 127 | 139 | 76 |
| DL | 100 | 220 | 159 | 147 | 119 |
| GL | 100 | 389 | 365 | 316 | 188 |

EXAMPLE 5

Comparative Efficacy of Lectin Preparations on HSPC Preservation:

The experiments described above were carried out on different samples as the yield of CD34+ cells from individual samples is not enough to carry out experiments with all lectins as a set and thus it was not possible to compare their efficacy. We therefore earned out experiment on CD34+ cells isolated from single CB samples which yielded enough CD34+ cells for such experiment using the optimal concentrations of 100 and 200 pg/ml. (N=2) It was observed that the number of CFU per $10^4$ incubated cells was not significantly different in various sets (FIG. 2 a) but when the data were normalized for total number of progenitors preserved the effect of lectins over control was evident (FIG. 2b). This analysis indicates that probably the lectins preserved more number of HSPC but probably did not affect the frequency of clonogenic cells. In this particular experiment BL at 100 pg/ml and DL at both 100 and 200 pg/ml were found to be more effective.

TABLE 3

Comparative Efficacy of Lectins

| Lectin conc. Used | Total progenitors preserved by | | | |
|---|---|---|---|---|
| | AL | BL | DL | GL |
| Cells | 337 | 337 | 337 | 337 |
| 100 pg/ml | 407 | 665 | 769 | 462 |
| 200 pg/ml | 382 | 560 | 708 | 585 |

TABLE 4

Comparative Efficacy of Lectins Expressed as Percent of Control

| Lectin conc. used | Total progenitors preserved by | | | |
|---|---|---|---|---|
| | AL | BL | DL | GL |
| Cells | 100 | 100 | 100 | 100 |
| 100 pg/ml | 121 | 197 | 228 | 137 |
| 200 pg/ml | 113 | 166 | 210 | 174 |

EXAMPLE 6

Determination of Specificity of the Lectin Action:

We have used mannose-biding lectins in this set of experiments. We therefore set experiments using Methyl α Mannoside in the incubation medium to see if this specific sugar abolishes the HSPC preservation activity of the lectins. CD34+ cells were incubated with BL or GL (100 and 200 pg/ml) with or without methyl α mannoside sugar (20 mM) for 10 days. It was observed that presence of the sugar abrogated the HSPC preservation activity of both BL and GL as seen by the near control colony formation in the sets with sugar while significant preservation activity was observed with lectins. (FIGS. 3 A and B).

EXAMPLE 7

Effect of Lectins on Preservation of LTC-IC:

In order to examine whether the lectins also preserved early progenitors we carried out the LTC-IC assay on CD34+ cells incubated with the optimal concentrations of lectins (100 and 200 pg/ml) for 30 days. After the incubation with lectins the surviving cells were seeded on irradiated (8000 rads) M210B4 feeder layer using Myelo-cult medium. The cultures were maintained for 5 weeks with weekly demi-defoliation. After 5 weeks the cultures were harvested by trypsinization. Both adherent and non-adherent cells were pooled and CFU assay was carried out. It was observed (FIGS. 4 A and B) that all lectins could preserve early progenitors up to 30 days of incubation.

Advantages:

1. The invention provides a simple cost effective method for preservation of hematopoietic stem progenitor cells in culture.
2. The invention provides a tool to study signaling mechanisms involved in the maintenance of quiescence in HSPC.
3. The invention provides a method to enrich the HSC for further manipulations.

We claim:

1. A method for preservation of human hematopoietic stem/progenitor cells, wherein the said method comprising the step of:
    a) providing a plurality of purified lectins selected from the group consisting of garlic lectin (GL), Mus a paradisiacal lectin (BL) and *Artocarpus integrifolia* lectin (AL) by dialyzing against phosphate buffered saline followed by filtration through 0.2 to 0.5 micron filter followed by protein determination using a micro bicinchonic assay (BCA) kit to check protein loss;
    b) isolating a plurality of CD34+ cells from a human cord blood sample;
    c) incubating of the isolated CD34+ cells obtained from step (b) with different concentration of the purified lectins in ranges between 100 pg/ml to 10 ng/ml for a period of 10 to 30 days followed by a toxicity test;
    d) subjecting incubated CD34+ cells obtained from step (c) to a CFU assay or seeding on an irradiating M210B4 feeder for LTC-IC assays; and
    e) interpreting the effect of the purified lectins on human hematopoietic stem/progenitor cells preservation.

2. The method as claimed in claim 1, wherein an aliquot of lectin is kept at about 4° C.

3. The method as claimed in claim 1, wherein the human cord blood sample is collected in a sterile bottle containing 40 IU of heparin as an anticoagulant per ml to 5 ml of a plain medium followed by the separation of a red blood cell and a mononuclear cell fraction by HES in a ratio range from 4 ml of cord blood to 1 ml of HES through a density gradient.

4. The method as claimed in claim 1, wherein a mononuclear cell (MNC) is suspended in an isolation buffer comprising 0.6% Na-citrate and 2% BSA in PBS and isolating the plurality of CD34+ cells is performed by immunomagnetic separation.

5. The method as claimed in claim 1, wherein the toxicity test is carried out on a plurality of TF1 cells using a MTT or a XTT assay.

6. The method as claimed in claim 1, wherein the incubated CD34$^+$ cells are tested for a number of progenitors preserved by scoring for different types of colonies in a semisolid methylcellulose medium comprising 1% Methyl cellulose+Plain IMDM+FBS 30%+Na-Pyruvate 10μM+Transferrin+μMercapto ethanol+BSA containing a standard growth factor qualified for a human clonogenic cell by using a standard criteria.

7. The method as claimed in claim 1, wherein a number of progenitors preserved by the lectins is estimated by obtaining a CFU from recovered cells after incubation with the lectins and calculating a total number of progenitors preserved by the lectins by normalizing with an input to provide primary screen for the lectins.

8. The method as claimed in claim 1, further comprising seeding the incubated CD34$^+$ cells on 8000 rads-irradiated M210B4 feeder layer formed on collagen coated wells using a Myelocult medium followed by maintaining the culture for 5-6 weeks by weekly demi-defoliation.

9. The method as claimed in claim 1, further comprising harvesting of the CD34$^+$ cells is carried out by trypsinization.

10. The method as claimed in claim 1, further comprising categorizing an adherent population and a non-adherent population from the CD34$^+$ cells to assay colony formation.

11. The method as claimed in claim 1, wherein the plurality of purified lectins is provided by dialyzing against a phosphate buffered saline (10 mM, pH7.4) followed by filtration through a 0.2 micron filter followed by determining protein loss.

* * * * *

UNITED STATES PATENT AND TRADEMARK OFFICE
CERTIFICATE OF CORRECTION

PATENT NO. : 8,859,282 B2
APPLICATION NO. : 12/096292
DATED : October 14, 2014
INVENTOR(S) : Vaijayanti P. Kale et al.

Page 1 of 1

It is certified that error appears in the above-identified patent and that said Letters Patent is hereby corrected as shown below:

Title Page, Column 2, References Cited OTHER PUBLICATIONS, Line 9, delete "hematopietic" and insert -- hematopoietic --

Title Page, Column 2, References Cited OTHER PUBLICATIONS, Line 13, delete "oligosaccarides" and insert -- oligosaccharides --

In the Claims

Column 8, Line 39, Claim 1, delete "bicinchonic" and insert -- bicinchoninic --

Column 9, Line 17, Claim 8, delete "M210B4feeder" and insert -- M210B4 feeder --

Signed and Sealed this
Third Day of February, 2015

Michelle K. Lee
*Deputy Director of the United States Patent and Trademark Office*